United States Patent [19]

Schroeder et al.

[11] 3,996,251
[45] Dec. 7, 1976

[54] PREPARATION OF PURE 1,5-DINITROANTHRAQUINONE

[75] Inventors: Bernd Schroeder, Odenthal; Wolfgang Auge; Karl-Werner Thiem, both of Cologne; Rutger Neeff, Leverkusen, all of Germany

[73] Assignee: Bayer Aktiengesellschaft, Leverkusen, Germany

[22] Filed: Apr. 1, 1976

[21] Appl. No.: 672,688

[30] Foreign Application Priority Data

Apr. 19, 1975  Germany ............................ 2517436

[52] U.S. Cl. ................................................ 260/369
[51] Int. Cl.² ........................ C07C 79/37; C09B 1/00
[58] Field of Search ...................................... 260/369

[56] References Cited

UNITED STATES PATENTS 3,786,073   1/1974   Frey et al. ........................... 260/369

Primary Examiner—Paul F. Shaver
Attorney, Agent, or Firm—Burgess, Dinklage & Sprung

[57] ABSTRACT

A mixture of dinitroanthraquinones of which at least 35% is 1,5-dinitroanthraquinone is dissolved at elevated temperature in a halogenated aromatic hydrocarbon, a carboxylic acid nitrile or a cyclic sulphone and is thereafter cooled selectively to precipitate substantially pure 1,5-dinitroanthraquinone. Preferred solvents are 1-chloronaphthalene, sulpholane and adipic acid dinitrile. The temperature of dissolution ranges from about 120° C up to the boiling point and cooling is by about 10° to 200° C to a temperature not below about 0° C.

10 Claims, No Drawings

PREPARATION OF PURE 1,5-DINITROANTHRAQUINONE

The present invention relates to a process for the preparation of pure 1,5-dinitroanthraquinone.

The complete nitration of anthraquinone to dinitroanthraquinones in sulphuric acid with nitric acid (Hefti; Helv. 14, page 1404 (1931)) and in pure nitric acid (Böttger and Petersen, Ann. 166, page 154 (1881)) gives mixtures of dinitroanthraquinones which essentially consist of 1,5-, 1,8-, 1,6- and 1,7-dinitroanthraquinones. 1,5- and 1,8-dinitroanthraquinones are important intermediate products for the preparation of dyestuffs (see Colour Index 65,405, 65,415, 69,015 and 70,510). A prerequisite for this, however, is that they are as free as possible from 1,6- and 1,7-dinitroanthraquinones.

It is known to separate off 1,5-dinitroanthraquinone from mixtures of dinitroanthraquinones by treatment with certain aromatic hydrocarbons which contain nitro groups, such as nitrobenzene or nitrotoluene. However, in this way, 1,5-dinitroanthraquinone is obtained only in a purity of 93.5%. German published specification DAS No. 2,248,704 or 95.3% (Japanese laid-open patent application No. 49.76851).

It has now been found that even purer 1,5-dinitroanthraquinone can be separated off in a technically advantageous manner from mixtures of dinitroanthraquinones which contain at least about 35% by weight of 1,5-dinitroanthraquinone when such mixtures are treated with a solvent at elevated temperature and cooled, and the 1,5-dinitroanthraquinone which is obtained as a residue is separated off, and isolated, in a manner which is in itself known.

Mixtures of dinitroanthraquinones which contain at least 35% by weight of 1,5-dinitroanthraquinone can be obtained in a manner which is in itself known from the nitration of anthraquinone and/or 1-nitroanthraquinone, for example with nitric acid alone or with a mixture of nitric acid and sulphuric acid. The preparation of such mixtures is described, for example, in German published specification DOS No. 2,143,253 or German Published Sepcification DOS 2,306,611. The reaction conditions, such as the temperature, the molar ratio of nitric acid:anthraquinone or the concentrations of nitric acid, under which these mixtures have been obtained are not critical for use of the mixtures within the scope of the process according to the invention. Thus, it is also possible for these mixtures to have been made up by deliberate mixing of the reaction products from different nitrations of anthraquinone or from the stages of their working up. In general, such mixtures also contain, in addition to 1,5-dinitroanthraquinone, 1,8-, 1,6- and 1,7-dinitroanthraquinone and, in some cases, also minor amounts of 2-nitroanthraquinone, 1-nitroanthraquinone and anthraquinone. Preferably, the mixture of dinitroanthraquinones employed in the process according to the invention contains at least about 50% by weight of 1,5-dinitroanthraquinone.

Possible solvents which can be employed within the scope of the process according to the invention are aromatic hydrocarbons, for example with 6 to 10 C atoms, which are monosubstituted or polysubstituted by halogen. Examples which may be mentioned are: o-dichlorobenzene, 1,2,3-trichlorobenzene, 1,2,4-trichlorobenzene and chloronaphthalenes, such as 1-chloronaphthalene.

Further solvents which can be used are nitriles which are derived from aromatic or aliphatic monocarboxylic acids or dicarboxylic acids with, for example, 3 to 8 C atoms, preferably those with 5 to 7 C atoms. Examples which may be mentioned are: benzonitrile, adipic acid dinitrile, malonic acid dinitrile, succinic acid dinitrile, glutaric acid dinitrile and pimelic acid dinitrile.

Other solvents which can be employed within the scope of the process according to the invention are cyclic sulphones, for example tetramethylenesulphone (sulpholane), pentamethylenesulphone, 2-methyl-tetramethylenesulphone and hexamethylenesulphone.

Solvents which are preferably employed are: sulpholane, 1-chloronaphthalene and adipic acid dinitrile.

In general, the process according to the invention is carried out by initially introducing the particular solvent at elevated temperature and stirring in the mixture of dinitroanthraquinones which is to be separated. The solvent is generally employed in a 2-fold to 8-fold amount, based on the amount of the mixture of dinitroanthraquinones which is employed. Elevated temperature is generally understood as temperatures of about 120° C up to the boiling point of the particular solvent used, temperatures of about 140° C up to 20° C below the boiling point of the particular solvent used being preferred. After all of the mixture of dinitroanthraquinones has been introduced, the mixture is advantageously left at elevated temperature, while stirring, for a certain time, generally 30 to 240 minutes. It is then cooled. In general, the mixture can be cooled by 10°–200° C, but as a rule not below 0° C. Preferably, the mixture is cooled by 10°–150° C and to temperatures not below 20° C. The pure 1,5-dinitroanthraquinone which is obtained as a residue can be isolated in a manner which is in itself known, for example by simple filtration.

The process according to the invention can be carried out both under normal pressure and also under elevated or reduced pressure. In general, however, the reaction will be carried out under normal pressure.

1,5-Dinitroanthraquinone can be obtained in purities of 98% by weight and above by the process according to the invention.

In the following Examples percentages are percentages by weight.

EXAMPLE 1

Anthraquinone is nitrated in sulphuric acid according to German published specification DOS No. 2,143,253 and the undissolved 1,5-dinitroanthraquinone is separated off by adjusting the $SO_3$ content of the nitration mixture to 8 to 20% and filtering the mixture.

40 g of a 1,5-dinitroanthraquinone fraction (analysis: 88% of 1,5-dinitroanthraquinone and 12% of 1,8-dinitroanthraquinone) obtained according to this process are stirred in 160 g of sulpholane for 3 hours at 150° C. The mixture is allowed to cool to 25° to 30° C in the course of 30 minutes and is stirred at this temperature for a further 1 hour and filtered. The filter cake is pressed off well and washed with methanol until free from sulpholane. 34 g of 1,5-dinitroanthraquinone are obtained.

(Purity. 98.3%, yield 95% of theory).

EXAMPLE 2

40 g of the 1,5-dinitroanthraquinone fraction used in Example 1 are stirred in 160 g of 1-chloronaphthalene for 4 hours at 170° C. The mixture is allowed to cool to 80° C and is stirred at this temperature for a further hour and filtered through a sintered glass suction filter which can be heated to 80° C. The filter cake is then pressed off well and, after cooling, washed with methanol until free from 1-chloronaphthalene. After drying, 33.5 g of 1,5-dinitroanthraquinone are obtained.

(Purity 98%, yield: 93% of theory)

EXAMPLE 3

If the procedure of Example 2 is followed but adipic acid dinitrile is used in place of 1-chloronaphthalene, 1,5-dinitroanthraquinone in a purity of 98.1 and a yield of 92% of theory is obtained.

EXAMPLE 4

208 g of anthraquinone and 955 g of 99% strength nitric acid (molar ratio of nitric acid to anthraquinone, 15:1) are heated to 35° C for 14 hours. 4,615 g of 91% strength nitric acid (mole fraction 0.76) are added to the warm reaction mixture. The 1,5-dinitroanthraquinone fraction (a) which has precipitated is separated off at room temperature, while 1,8-dinitroanthraquinone (b) is precipitated from the filtrate by distilling off 3,050 g of 99% strength nitric acid (mole fraction 0.57) and is then separated off.

a. Yield: 79 g (26% of theory), 91.2% of 1,5-dinitroanthraquinone and 7.9% of 1,8-dinitroanthraquinone b. Yield: 145 g (48% of theory), 29.6% of 1,5-dinitroanthraquinone and 70.1% of 1,8-dinitroanthraquinone.

40 g of fraction (a) are treated analogously to Example 1. This gives 35.4 g of a 98.1% pure 1,5-dinitroanthraquinone. (Yield: 95% of theory).

EXAMPLE 5 and 6

If fraction (a) of Example 4 is treated with 1-chloronaphthalene or adipic acid dinitrile analogously to Example 2 and 3, a 1,5-dinitroanthraquinone of about 98% purity is again obtained. The yields are between 92 and 95% of theory.

EXAMPLE 7

50 g of a mixture of dinitroanthraquinones, which contain 51.1% of 1,5-dinitroanthraquinone and 48.6% of 1,8-dinitroanthraquinone, are stirred in 200 g of sulpholane for 3 hours at 170° C. The mixture is allowed to cool to 140° C in the course of 30 minutes and is stirred for a further 1.5 hours at this temperature and then filtered through a sintered glass suction filter which is pre-heated to 140°. The filter cake is pressed off well and treated with sulpholane, as described in Example 1. 20.5 g of a 98.1% pure 1,5-dinitroanthraquinone are obtained.

(Yield: 78.8% of theory).

EXAMPLE 8

30 g of a mixture of dinitroanthraquinones (51.1% of 1,5-dinitroanthraquinone and 48.6% of 1,8-dinitroanthraquinone) are stirred in 180 g of 1-chloronaphthalene for 1 hour at 210° C. The mixture is allowed to cool to 180° C in the course of 30 minutes and is filtered, at this temperature, through a pre-heated sintered glass suction filter and the material on the filter is washed with 30 g of hot 1-chloronaphthalene at 180° C. The product thus obtained is treated again with 1-chloronaphthalene, analogously to Example 2. This gives 10.7 g of the product (98.3% by weight of 1,5-dinitroanthraquinone, yield: 68.4% of theory).

EXAMPLE 9

40 g of a mixture consisting of 50% of 1,5-dinitroanthraquinone and 50% of 1,8-dinitroanthraquinone are stirred in 200 g of adipic acid dinitrile for 1 hour at 180° C, and, after cooling to 170° C, the mixture is filtered, through a preheated sintered glass suction filter. The material on the filter is washed with 40 g of hot adipic acid dinitrile and then with methanol.

After drying, the residue gives 14.8 g of a 99.7% pure 1,5-dinitroanthraquinone.

(Yield: 73.8% of theory).

It will be appreciated that the instant specification and examples are set forth by way of illustration and not limitation, and that various modifications and changes may be made without departing from the spirit and scope of the present invention.

What is claimed is:

1. A process for separating off 1,5-dinitroanthraquinone from a mixture of dinitroanthraquinones which contains at least about 35% by weight of 1,5-dinitroanthraquinone, which comprises dissolving such mixture at elevated temperature in a solvent selected from the group consisting of a halogenated aromatic hydrocarbon, a nitrile of an aromatic or aliphatic carboxylic acid and a cyclic sulphone, cooling the solution thereby selectively precipitating the 1,5-dinitroanthraquinone, and separating the precipitated 1,5-dinitroanthraquinone from the solution.

2. The process according to claim 1, in which the mixture of dinitroanthraquinones contains at least about 50% by weight of 1,5-dinitroanthraquinone.

3. The process according to claim 1, wherein said solvent is a chlorobenzene or chloronaphthalene.

4. The process according to claim 1, wherein said solvent is 1-chloronaphthalene.

5. The process according to claim 1, wherein said solvent is the nitrile of an aliphatic or aromatic mono- or dicarboxylic acid having from 3 to 8 carbon atoms.

6. The process according to claim 5, wherein said solvent is adipic acid dinitrile.

7. The process according to claim 1, wherein said solvent is an optionally methyl-substituted tetra-, penta- or hexa-methylene sulphone.

8. The process according to claim 7, wherein said solvent is sulpholane.

9. The process according to claim 1, wherein the dissolution in the solvent is carried out at a temperature from about 120° C up to the boiling point of the solvent and the mixture is then cooled by about 10° to 200° C to a temperature not below about 0° C.

10. The process according to claim 2, wherein the solvent is selected from the group consisting of 1-chloronaphthalene, adipic acid dinitrile and sulpholane, the dissolution in the solvent is carried out at a temperature from about 140° C up to about 20° C below the boiling point of the solvent and the mixture is then cooled by about 10° to 150° C to a temperature not below about 20° C.

* * * * *